United States Patent
Baba et al.

(10) Patent No.: US 9,079,124 B2
(45) Date of Patent: Jul. 14, 2015

(54) PRESACCHARIFICATION TREATMENT DEVICE FOR LIGNOCELLULOSIC BIOMASS

(75) Inventors: Tsuyoshi Baba, Saitama (JP); Junji Yasuda, Saitama (JP)

(73) Assignee: HONDA MOTOR CO., LTD., Tokyo (JP)

(*) Notice: Subject to any disclaimer, the term of this patent is extended or adjusted under 35 U.S.C. 154(b) by 427 days.

(21) Appl. No.: 13/808,207

(22) PCT Filed: Jun. 27, 2011

(86) PCT No.: PCT/JP2011/064653
§ 371 (c)(1),
(2), (4) Date: Jan. 3, 2013

(87) PCT Pub. No.: WO2012/005131
PCT Pub. Date: Jan. 12, 2012

(65) Prior Publication Data
US 2013/0112191 A1   May 9, 2013

(30) Foreign Application Priority Data
Jul. 5, 2010  (JP) .................................. 2010-153330

(51) Int. Cl.
 *B01D 11/04*  (2006.01)
 *C13K 1/02*  (2006.01)
(52) U.S. Cl.
 CPC . *B01D 11/04* (2013.01); *C13K 1/02* (2013.01); *C12P 2201/00* (2013.01)
(58) Field of Classification Search
 CPC ........ B01D 11/04; C12P 2201/00; C13K 1/02
 See application file for complete search history.

(56) References Cited

U.S. PATENT DOCUMENTS 8,444,925 B2 * 5/2013 Baba .............................. 422/198
2009/0053770 A1 2/2009 Hennessey et al.

FOREIGN PATENT DOCUMENTS

| JP | 57-005697 A | 1/1982 |
| JP | 2005-232453 A | 9/2005 |

(Continued)

OTHER PUBLICATIONS

Written Opinion of the International Searching Authority for PCT/JP2011/064653, dated Aug. 9, 2011.*
Elizabeth (Newton) Sendich et al., "Recent Process and Resulting Reductions in Minimum Ethanol Selling Price", Bioresource Technology, 2008, vol. 99, pp. 8429-8435.

(Continued)

*Primary Examiner* — David A Reifsnyder
(74) *Attorney, Agent, or Firm* — Rankin, Hill & Clark LLP

(57) ABSTRACT

[Problems to be Solved] Provided is a presaccharification treatment device, which can yield from lignocellulosic biomass as a substrate a presaccharification treatment product without heating and thereby at a reduced cost.
[Solution] A presaccharification treatment device (1) comprises a treatment unit (2), which mixes lignocellulosic biomass and ammonia water and treats a yielded substrate mixture in a wet powder state for yielding a presaccharification treatment product, and an ammonia separation unit (3), which separates ammonia from the presaccharification treatment product. The treatment unit (2) comprises a treatment vessel (21) and a storage unit (25), in which a presaccharification treatment product is yielded during retention therein for a predetermined time period from the substrate mixture without heating. The ammonia separation unit (3) is installed direct below the storage unit (25).

4 Claims, 2 Drawing Sheets

(56) References Cited

FOREIGN PATENT DOCUMENTS

| | | |
|---|---|---|
| JP | 2008-535524 A | 9/2008 |
| JP | 2010-115162 A | 5/2010 |
| WO | WO 2006110900 A2 | 10/2006 |
| WO | WO 2009/045654 A2 | 4/2009 |
| WO | WO 2010/035832 A1 | 4/2010 |

OTHER PUBLICATIONS

Tae Hyun Kim et al., "Pretreatment and Fractionation of Corn Stover by Ammonia Recycle Percolation Process", Bioresource Technology, 2005, vol. 96, pp. 2007-2013.

* cited by examiner

PRESACCHARIFICATION TREATMENT DEVICE FOR LIGNOCELLULOSIC BIOMASS

CROSS-REFERENCE TO RELATED APPLICATION

This application is a National Stage entry of International Application No. PCT/JP2011/064653 filed Jun. 27, 2011, which claims priority to Japanese Patent Application No. 2010-153330 filed Jul. 5, 2010, the disclosure of the prior applications are hereby incorporated in their entirety by reference.

TECHNICAL FIELD

The present invention relates to a presaccharification treatment device for lignocellulosic biomass.

BACKGROUND ART

A process for producing ethanol, by which lignocellulosic biomass such as rice straw as a substrate is saccharified by a saccharifying enzyme produced by a microorganism and then the yielded saccharide is fermented, has been heretofore known. In this regard, lignocellulosic biomass is constituted such that lignin is bound to cellulose or hemicellulose firmly. Consequently, a presaccharification treatment product is used, which is prepared by pretreating lignocellulosic biomass to dissociate lignin contained in the lignocellulosic biomass or to swell the lignocellulosic biomass, for saccharification.

In this regard, the term "dissociate" means herein at least a part of the bonds between lignin and cellulose or hemicellulose is broken. The term "swell" means that crystalline cellulose expands due to infiltration of a liquid, which generates gaps in cellulose or hemicellulose constituting the crystalline cellulose, or gaps inside a cellulose fiber.

Since a saccharifying enzyme is expensive, it has been common in a conventional ethanol production process that the concentration of a substrate contained in a presaccharification treatment product is set at a low level in order to save the consumption of a saccharifying enzyme. However, if the concentration of a substrate contained in a presaccharification treatment product is set at a low level, the resulted concentration of a saccharified solution to be yielded from such a presaccharification treatment product becomes also low, and as a consequence, the concentration of ethanol to be yielded by fermenting the saccharified solution becomes also low. As a result, there occurs a problem that the time and thermal energy required for distillation increase, when the yielded ethanol is distilled to be concentrated.

To solve the problem, it is conceivable to increase the concentration of a substrate contained in a presaccharification treatment product, and also increase the consumption of a saccharifying enzyme, so as to yield ethanol at a high concentration. In this case, however, the cost increases due to the increase in the consumption of an expensive saccharifying enzyme, the cost of the process for producing ethanol as a whole is required to be reduced.

Streamlining of a presaccharification treatment for lignocellulosic biomass is conceivable as a measure for reducing cost in an ethanol production process.

As a presaccharification treatment process for lignocellulosic biomass, a process by which, for example, lignocellulosic biomass is mixed with liquid pure ammonia, heated, pressurized, and then rapidly depressurized, has been known. By doing so, vaporized ammonia gas expands rapidly, so that the lignocellulosic biomass also expands and lignin is removed physically from the lignocellulosic biomass (see Patent Literature 1).

However, use of pure ammonia requires special devices, such as a high pressure container for storage, and therefore use of ammonia water, which is an aqueous solution of pure ammonia, has been studied.

As a process for using ammonia water, a process, by which lignocellulosic biomass is brought into contact with ozone and then immersed in ammonia water, has been known (see Patent Literature 2). In this case, however, a device for contacting lignocellulosic biomass with ozone is necessary, and a process step therefor is added, and consequently the cost cannot necessarily be reduced.

Further, a process, by which a mixture obtained by mixing lignocellulosic biomass and ammonia water is heated, has been known (see Patent Literature 3). According to a process of Patent Literature 3, if lignocellulosic biomass is dispersed in ammonia water with the concentration of 0.8 to 15% by weight and heated, lignin will be dissociated from lignocellulosic biomass or the lignocellulosic biomass will be swollen.

CITATION LIST

Patent Literature

Patent Literature 1: Japanese Patent Laid-Opened Publication No. 2005-232453
Patent Literature 2: Japanese Patent Laid-Opened Publication No. S57-5697
Patent Literature 3: Japanese National Publication of International Patent Application No. 2008-535524

SUMMARY OF INVENTION

Technical Problem

However, for conducting the process according to Patent Literature 3, there is a drawback that a device provided with a heating unit which supplies thermal energy for dissociating lignin from lignocellulosic biomass or swelling the lignocellulosic biomass is required.

Under such circumstances, an object of the present invention is to provide a presaccharification treatment device for lignocellulosic biomass, by which lignin can be dissociated from lignocellulosic biomass or lignocellulosic biomass can be swollen without supplying thermal energy and thereby eliminating said drawback and reducing the cost involved in a presaccharification treatment.

Solution to Problem

A presaccharification treatment device for lignocellulosic biomass according to the present invention comprises: a treatment unit configured to mix lignocellulosic biomass as a substrate and ammonia water, and then treat the yielded substrate mixture in a wet powder state to dissociate lignin contained in the substrate or to swell the substrate to yield a presaccharification treatment product in a wet powder state; and an ammonia separation unit configured to separate ammonia from the presaccharification treatment product; wherein the treatment unit comprises: a treatment vessel; a substrate supply unit configured to supply continuously the substrate to the treatment vessel; an ammonia water supply unit configured to supply continuously the ammonia water to the treatment vessel; a mixing unit configured to agitate the substrate and the ammonia water supplied to the treatment vessel to thereby apply shearing force and impact force to the substrate and to mix the ammonia water and the substrate to yield the substrate mixture; and a storage unit placed directly beneath the treatment vessel communicating with the treatment vessel and configured to store a substrate mixture supplied from the treatment vessel for a predetermined time period and to dissociate lignin contained in the substrate or to swell the substrate during storage without heating to yield a presaccharification treatment product; and wherein the ammonia separation unit comprises a presaccharification treatment product supply unit placed beneath the storage unit and configured to supply continuously the presaccharification treatment product from the storage unit to the ammonia separation unit, and is located directly beneath the storage unit.

In a presaccharification treatment device for lignocellulosic biomass (hereinafter occasionally abbreviated as "a presaccharification treatment device") according to the present invention, firstly, lignocellulosic biomass as a substrate and ammonia water are fed continuously to the treatment vessel from the substrate supply unit and the ammonia water supply unit respectively.

It is difficult to impregnate lignocellulosic biomass as a substrate uniformly with ammonia water by simple mixing with ammonia water, and heating is required for ammonia to act on such a substrate so as to dissociate lignin.

On the other hand, in a presaccharification treatment device according to the present invention, a substrate and ammonia water are continuously supplied to the treatment vessel and also agitated by the mixing unit, so that ammonia water and a substrate are mixed. Shearing force and impact force are thereby applied to the substrate, so that the substrate is uniformly impregnated with ammonia water to yield a substrate mixture in a wet powder state.

Then, the substrate mixture yielded in the mixing unit is fed to the storage unit communicating with the treatment vessel and stored. Since a substrate in the substrate mixture fed to the storage unit is uniformly impregnated with ammonia water, during storage in the storage unit, a reaction of ammonia for dissociating lignin from the substrate or swelling the substrate progresses without heating.

Next, a presaccharification treatment product stored in the storage unit is continuously fed from the storage unit to the ammonia separation unit by a presaccharification treatment product supply unit placed beneath the storage unit. Since a presaccharification treatment product stored in the storage unit is in a wet powder state, which is difficult to transport, the presaccharification treatment product is forcibly discharged from the storage unit by the presaccharification treatment product supply unit and fed continuously to the ammonia separation unit.

Then, ammonia is separated from the presaccharification treatment product by the ammonia separation unit to yield a presaccharification treatment product from which ammonia has been separated out.

According to a presaccharification treatment product according to the present invention, a presaccharification treatment product, in which lignin is dissociated from the substrate or the substrate is swollen, can be yielded without heating by storing a substrate mixture in the storage unit for a predetermined time period, and therefore the cost required for the presaccharification treatment can be reduced.

Further, in a presaccharification treatment device according to the present invention, the storage unit is placed directly beneath the treatment vessel and the ammonia separation unit is placed directly beneath the storage unit, transfer of a substrate mixture in a wet powder state, which is difficult to transfer, from the treatment vessel to the storage unit can be facilitated, and transfer of a presaccharification treatment product in a wet powder state, which is difficult to transfer, yielded from the substrate mixture, from the storage unit to the ammonia separation unit can be also facilitated. The costs involved in transferring the substrate mixture and the presaccharification treatment product can therefore be reduced to decrease the cost required for the presaccharification treatment.

Further, in a presaccharification treatment device according to the present invention, since ammonia is separated from the presaccharification treatment product by the ammonia separation unit, the consumption of a pH adjuster for regulating the pH of a presaccharification treatment product to be saccharified to an optimal pH value can be reduced.

Preferably in a presaccharification treatment device according to the present invention, the ammonia water supply unit supplies ammonia water with the concentration in the range of 20 to 30% by mass, and supplies the ammonia water at a mass ratio in the range of 1:0.7 to 1:1.3 with respect to the substrate supplied by the substrate supply unit.

By doing so, a substrate can be impregnated more uniformly with ammonia water in the mixing unit, and dissociation of lignin from the substrate or swelling of the substrate can be performed more easily.

In this regard, if the concentration of ammonia water is less than 20% by mass, dissociation of lignin from a substrate or swelling of a substrate may become insufficient. On the other hand, even if the concentration of ammonia water exceeds 30% by mass, no more effect can be obtained with respect to dissociation of lignin from a substrate or swelling of a substrate.

Further, if ammonia water to be added in an amount less than 0.7 parts by mass with respect to 1 part by mass of a substrate is, ammonia water is insufficient and the substrate may occasionally be not impregnated uniformly with ammonia water. As a result, dissociation of lignin from a substrate or swelling of a substrate may become insufficient.

On the other hand, even if ammonia water to be added with respect to 1 part by mass of a substrate exceeds 1.3 parts by mass, no more effect can be obtained with respect to dissociation of lignin from a substrate or swelling of a substrate.

Preferably, in a presaccharification treatment device according to the present invention, the ammonia separation unit heats the presaccharification treatment product by a heating medium for separating ammonia from the presaccharification treatment product; and the presaccharification treatment product and the heating medium flow in the ammonia separation unit in a counter current direction.

Since a presaccharification treatment product supplied to the ammonia separation unit evaporates off ammonia by being heated in the ammonia separation unit, the concentration of ammonia water in the presaccharification treatment product decreases from entry of the presaccharification treatment product into the ammonia separation unit until discharge therefrom. Further, if the concentration of ammonia water in the presaccharification treatment product decreases, the boiling point of the ammonia water increases.

Consequently, with respect to the ammonia separation unit, from entry of the presaccharification treatment product into the ammonia separation unit until discharge therefrom, it is necessary to make the temperature of the presaccharification treatment product flowing in the ammonia separation unit to a boiling point temperature corresponding to the concentration of ammonia water in order to separate adequately ammonia from the presaccharification treatment product.

In this context, since the presaccharification treatment product and the heating medium flow in a counter current direction in the ammonia separation unit, such temperature difference between the presaccharification treatment product and the heating medium as required for adequate separation of ammonia from the presaccharification treatment product can be realized from entry of the presaccharification treatment product into the ammonia separation unit until discharge therefrom to perform highly efficient heat exchange.

Notwithstanding the above, ammonia may be occasionally not separated adequately only by heating a presaccharification treatment product in the ammonia separation unit.

Therefore, it is preferable that with respect to a presaccharification treatment device according to the present invention, the ammonia separation unit comprises: an ammonia gas suction unit configured to suck ammonia gas vaporized from a presaccharification treatment product supplied into the ammonia separation unit; and a vacuum-retaining unit configured to be able to maintain a presaccharification treatment product moving in the ammonia separation unit under vacuum state by sucking the ammonia gas using the ammonia gas suction unit; and the vacuum-retaining unit comprises: an introducing unit configured to maintain a presaccharification treatment product in the ammonia separation unit under vacuum state, and to introduce a presaccharification treatment product supplied from the storage unit into the ammonia separation unit; and a discharging unit configured to maintain a presaccharification treatment product in the ammonia separation unit under vacuum state, and to discharge a presaccharification treatment product from which ammonia has been separated out from the ammonia separation unit.

As a result, a presaccharification treatment product can be transported in the ammonia separation unit, while maintaining it under vacuum state by the introducing unit and the discharging unit. Further, since ammonia gas vaporized from a presaccharification treatment product is sucked by the ammonia gas suction unit, ammonia can be separated adequately from the presaccharification treatment product.

DESCRIPTION OF EMBODIMENTS

An embodiment of the present invention will be described below in more detail referring to the appended drawings.

Figure 1:
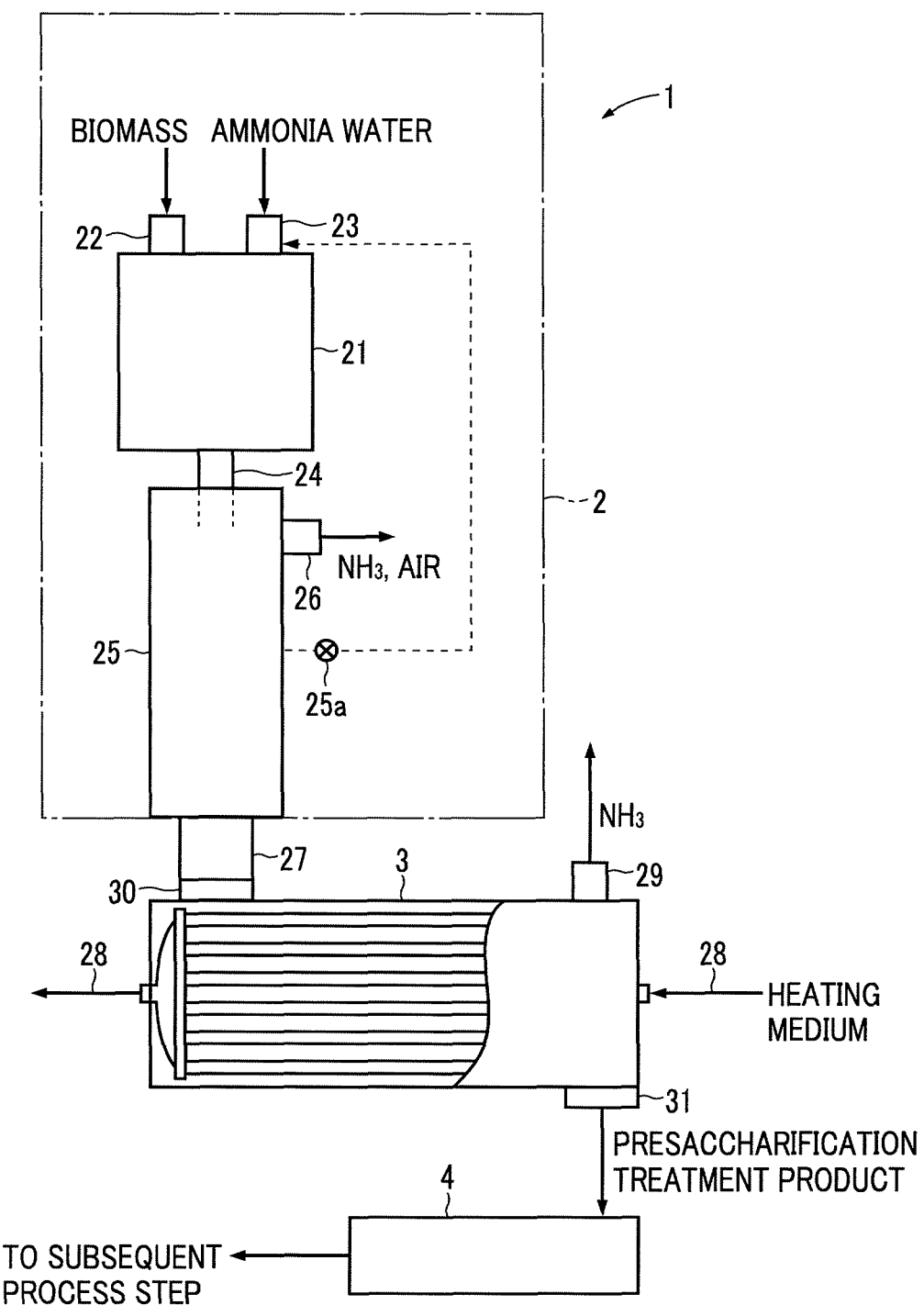
FIG. 1 is a block diagram showing a constitutional example of a presaccharification treatment device for lignocellulosic biomass according to the present invention.

As shown in FIG. 1 a presaccharification treatment device 1 for lignocellulosic biomass according to the current embodiment comprises a treatment unit 2, an ammonia separation unit 3, and a transfer unit 4. The treatment unit 2 is a device for preparing a substrate mixture by mixing lignocellulosic biomass as a substrate and ammonia water, and for yielding a presaccharification treatment product by dissociating lignin from the substrate in the substrate mixture or swelling the substrate. The ammonia separation unit 3 is a device for separating ammonia from the presaccharification treatment product. The transfer unit 4 is a device for transferring the presaccharification treatment product from which ammonia has been separated out to a subsequent enzymatic saccharification step.

According to the current embodiment, as lignocellulosic biomass as a substrate, for example, rice straw can be used.

The treatment unit 2 is equipped with a treatment vessel 21, and the treatment vessel 21 is equipped with a substrate supply unit 22 for supplying continuously a substrate and an ammonia water supply unit 23 for supplying continuously ammonia water. The treatment vessel 21 is equipped with a mixing unit (not illustrated), which agitates the substrate and the ammonia water to apply shearing force and impact force to the substrate, and mixes the ammonia water and the substrate.

Further, the treatment unit 2 is equipped with a silo 25, which is communicated with the treatment vessel 21 through a line 24, supplied with the substrate mixture yielded in the treatment vessel 21 by mixing the ammonia water and the substrate, and stores the substrate mixture as a storage unit. The silo 25 is located directly beneath the treatment vessel 21. The lower end of the line 24 is inserted into the silo 25 and an outlet discharging the substrate mixture is opened inside the silo 25.

In the silo 25 by storing the substrate mixture for a predetermined time period without heating, lignin is dissociated from the substrate or the substrate is swollen to yield a presaccharification treatment product. Further, the silo 25 is equipped with a level meter 25a for detecting the surface of a substrate mixture and a presaccharification treatment product in the silo 25.

The silo 25 is provided with an exhaust port 26 at the upper part. The exhaust port 26 has a function to vent out ammonia gas and air having entrained with the substrate mixture supplied from the treatment vessel 21.

The ammonia separation unit 3 is provided with a heating multi-tube bundle in a shell as shown in FIG. 1, and heats a presaccharification treatment product supplied to the ammonia separation unit 3 by introducing a heating medium into the tubes of the heating multi-tube bundle. The ammonia separation unit 3 is located directly beneath the silo 25.

The ammonia separation unit 3 is equipped with a powder feeder 27 as a presaccharification treatment product supply unit, which supplies forcibly the presaccharification treatment product yielded in the silo 25 at a predetermined amount continuously to the ammonia separation unit 3. The powder feeder 27 is located directly beneath the silo 25 and connected directly to the silo 25.

The ammonia separation unit 3 is connected with a heating medium feed line 28 to feed a heating medium for heating the presaccharification treatment product in the ammonia separation unit 3. As a heating medium, for example, steam or hot water may be used. Further, the ammonia separation unit 3 is so constituted that a presaccharification treatment product and a heating medium flow therein in a counter current direction.

Further, the ammonia separation unit 3 is equipped with an ammonia gas suction unit 29, which sucks ammonia gas vaporized from a presaccharification treatment product in the ammonia separation unit 3. As the ammonia gas suction unit 29, for example, a vacuum pump may be used.

Further, the ammonia separation unit 3 is equipped with an introducing unit 30 directly connected with a powder feeder 27 and introducing a presaccharification treatment product supplied from the silo 25 through the powder feeder 27 into the ammonia separation unit 3, and a discharging unit 31 located opposite to the introducing unit 30 with respect to the shell of the ammonia separation unit 3 and discharging the presaccharification treatment product from which ammonia has been separated out from the ammonia separation unit 3.

The introducing unit 30 and the discharging unit 31 have also a function as a vacuum-retaining unit, which can retain the presaccharification treatment product in the ammonia separation unit 3 under vacuum state by sucking ammonia gas using the ammonia gas suction unit 29. As the introducing unit 30 or the discharging unit 31, for example, a rotary valve can be used.

Figure 2:
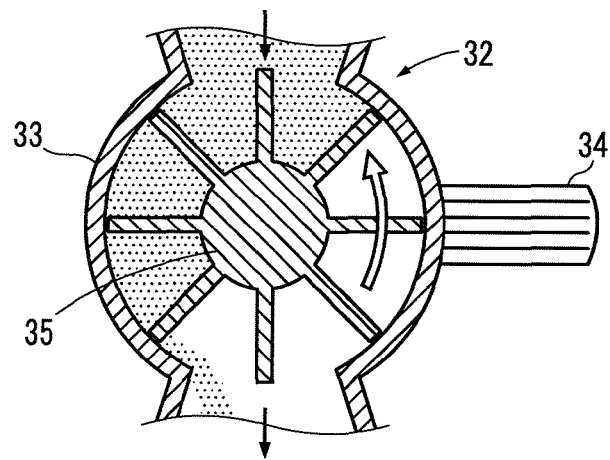
FIG. 2 is an illustrative sectional view of an example of the vacuum-retaining unit to be used in the presaccharification treatment device for lignocellulosic biomass shown in FIG. 1.

FIG. 2 shows a rotary valve, which can be used as the introducing unit 30 or the discharging unit 31 according to the current embodiment. The rotary valve 32 has in a rotary valve case 33 a rotor 35, which is driven by an electric motor 34 to rotate, and transports a presaccharification treatment product filled into the rotor 35 from the upper side by rotation downward, and discharges and supply the same.

Even if there exists a pressure difference between the upper side and the lower side of the rotor 35, the rotary valve 32 can transport the presaccharification treatment product from the upper side to the lower side of the rotor 35, while maintaining the pressures at the upper side and the lower side of the rotor 35.

Next, the operation of the pretreatment device 1 according to the current embodiment will be described.

With respect to the pretreatment device 1, in the treatment unit 2, a substrate is continuously fed from the substrate supply unit 22 to the treatment vessel 21 and also ammonia water is continuously fed from the ammonia water supply unit 23 to the treatment vessel 21. According to the current embodiment, as the substrate supply unit 22 a metering feeder is used, which can feed a substrate quantitatively, and as the ammonia water supply unit 23 a feed pump is used, which can regulate the flow rate.

As a substrate, for example, rice straw may be used. Rice straw is chopped by, for example, a cutter mill (not illustrated) to approx. 3 mm long. As for supply quantity of a substrate according to the current embodiment, the supply quantity of the substrate corresponding to the supply quantity of a presaccharification treatment product supplied from the silo 25 to the ammonia separation unit 3 by the powder feeder 27 is supplied to the treatment vessel 21 through the substrate supply unit 22.

Further, as ammonia water, according to the current embodiment, that with the concentration in the range of 20 to 30% by mass, for example, with the concentration of 25% by mass is used. In supplying ammonia water, the ammonia water supply unit 23 supplies ammonia water in the range of 0.7 to 1.3 parts by mass, preferably 1 part by mass, with respect to 1 part by mass of a substrate supplied by the substrate supply unit 22.

The substrate and the ammonia water supplied as above are agitated in the treatment vessel 21 to mix the ammonia water and the substrate to a substrate mixture in a wet powder state. During such an operation, impact force due to a collision with ammonia water supplied concurrently, a collision between the substrate itself, or a collision between the substrate and the treatment vessel 21 and the like, as well as shearing force due to agitation are applied to the substrate. As a result, ammonia water is impregnated uniformly in the substrate.

Then, the substrate mixture is discharged continuously from the treatment vessel 21 and fed to the silo 25 through the line 24. In such a operation, the substrate mixture is in a wet powder state, while the silo 25 is placed directly beneath the treatment vessel 21, and the lower end of the line 24 is inserted into the silo 25. Consequently, an outlet discharging the substrate mixture from the line 24 is opened inside the silo 25 to prevent the substrate mixture from splashing around. Further, by shortening the length of the line 24, the substrate mixture can be fed to the silo 25 without occluding the line 24 by causing bridging.

Meanwhile, ammonia gas or air may come in together with a substrate mixture into the silo 25. The ammonia gas and air are vented out of the silo 25 through the exhaust port 26 placed at an upper part of the silo 25, and therefore do not disturb storage of the substrate mixture in the silo 25 and the internal space of the silo 25 can be utilized effectively for storing the substrate mixture.

According to the current embodiment, as the treatment vessel 21, for example, a mixer 41 (Trade name: Spiral Pin Mixer (Model W), made by Pacific Machinery & Engineering Co., Ltd.) having the structure shown in FIG. 3 can be used. The mixer 41 is provided with a housing 44 composed of a top cover 42 in a flat plate form and a side wall 43 in an inverse-conical shape extending from the outer edge of the top cover 42 downward, and a powder feed port 45 and a liquid feed port 46 are provided concentrically at the center of the top cover 42. The housing 44 has internally a freely rotatable mixing rotor 47 and an outlet 48 opened at a part of the lower side of the side wall 43.

The mixing rotor 47 comprises a horizontal plane 49 facing the top cover 42 with a gap therebetween and an inclined plane 50 extending from the outer edge of the horizontal plane 49 downward facing the side wall 43 with a gap therebetween. The horizontal plane 49 is provided with a plurality of primary dispersing pins 51 in spirals, and the inclined plane 50 is provided with a plurality of secondary dispersing pins 52.

With respect to the mixer 41, the powder feed port 45 is connected with the substrate supply unit 22 and the liquid feed port 46 is connected with the ammonia water supply unit 23. The outlet 48 corresponds to the outlet of the line 24 and the mixing rotor 47 corresponds to the mixing unit.

With respect to the mixer 41, a substrate is continuously fed from the powder feed port 45 with the mixing rotor 47 rotating and ammonia water is continuously fed from the liquid feed port 46. By doing so, the ammonia water is spread along the horizontal plane 49 of the mixing rotor 47 in the outer circumferential direction; while the substrate is combined with the ammonia water on the horizontal plane 49 and is agitated thereby. The substrate further collides with the primary dispersing pins 51 while being agitated described above, which applies impact force and shearing force to the substrate.

Then, the substrate together with ammonia water flows down along the inclined plane 50 of the mixing rotor 47, but at the same time driven upward by the secondary dispersing pins 52. As a result, the ammonia water and the substrate are mixed together to form a substrate mixture, in which the substrate is uniformly impregnated with the ammonia water. The mixture is discharged continuously from the outlet 48.

Figure 3:
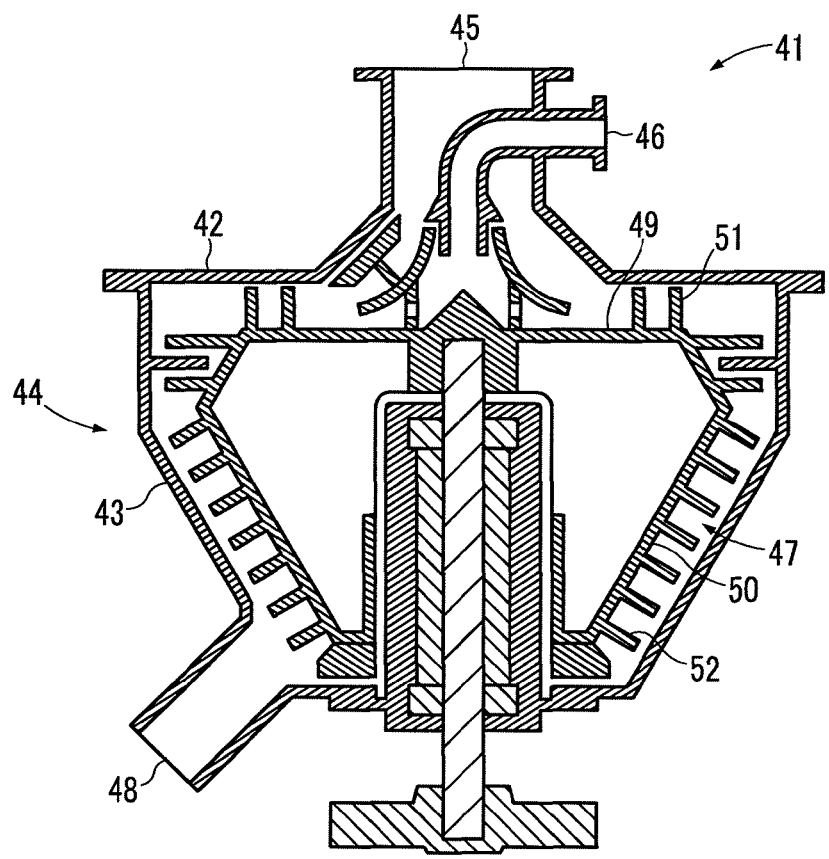
FIG. 3 is an illustrative sectional view of an example of the mixing unit to be used in the presaccharification treatment device for lignocellulosic biomass shown in FIG. 1.

The treatment vessel 21 is not limited to the mixer 41 shown in FIG. 3, insofar as it can agitate a substrate and ammonia water supplied so as to apply shearing force and impact force to a substrate, and mix the substrate and the ammonia water to form a substrate mixture. Examples of such a treatment vessel 21 include in addition to the mixer 41 shown in FIG. 3, a continuous jet mixer (e.g. Trade name: Flow Jet Mixer, made by Funken Powtechs, Inc.), and a friction grinder (e.g. Trade name: Supergrindel, made by Masuko Sangyo Co., Ltd.).

Next, with respect to the presaccharification treatment device 1, a substrate mixture supplied from the treatment vessel 21 to the silo 25 is retained in the silo 25. The substrate mixture goes through the silo 25 without heating, for example, at a temperature of 25° C. spending a time period in the range of 24 to 360 hours, e.g. 100 hours.

In this case, the substrate is impregnated uniformly with ammonia water having the concentration in the range of 20 to 30% by mass, e.g. 25% by mass in the range of 0.7 to 1.3 parts by mass, e.g. 1 part by mass, with respect to 1 part by mass of the substrate. During the substrate goes through the silo 25, due to the action of ammonia, lignin is dissociated from the substrate or the substrate is swollen. As a result, a presaccharification treatment product is yielded, in which lignin is dissociated from the substrate or the substrate is swollen.

Next, the presaccharification treatment product is taken out by the powder feeder 27 from the silo 25 continuously at a predetermined amount and fed to the ammonia separation unit 3. According to the current embodiment, a substrate corresponding to the supply quantity of a presaccharification treatment product of the powder feeder 27 is supplied by the substrate supply unit 22, and the supply amount of ammonia water to be supplied by the ammonia water supply unit 23 is controlled so as to keep the retained volume of the substrate mixture and the presaccharification treatment product in the silo 25 constant by detecting the surface of the same using the level meter 25a. Therefore, the material balance in the silo 25 is conserved and a stable continuous operation can be conducted.

Since it is difficult to discharge a presaccharification treatment product in a wet powder state, the powder feeder 27 is preferably placed directly beneath the silo 25, and equipped with a scraper, which has a function to scrape off forcibly the presaccharification treatment product and supply the same to the ammonia separation unit 3. Examples of such a powder feeder 27 include a continuous quantitative feeder (e.g. Trade name: Smooth Auto Feeder CF300, made by Taisei Mfg. Co., Ltd.).

Then, with respect to a presaccharification treatment product supplied by the powder feeder 27 to the ammonia separation unit 3, ammonia is separated from the presaccharification treatment product in the ammonia separation unit 3.

Since a presaccharification treatment product in the ammonia separation unit 3 evaporates ammonia by heating, the concentration of the ammonia water in the presaccharification treatment product decreases gradually and the boiling point of the ammonia water increases, when it is transferred by the introducing unit 30 and the discharging unit 31 from the side of the introducing unit 30 to the side of the discharging unit 31. According to the current embodiment, the presaccharification treatment product flows in the ammonia separation unit 3 in a counter current direction against the flow of a heating medium, and therefore the temperature of the presaccharification treatment product flowing in the ammonia separation unit 3 can be made equivalent to a boiling point temperature corresponding to a concentration of the ammonia water, so as to separate ammonia from the presaccharification treatment product.

Further, since the pressure in the ammonia separation unit 3 can be maintained by the introducing unit 30 and the discharging unit 31, ammonia can be separated adequately from a presaccharification treatment product by sucking ammonia gas vaporized from the presaccharification treatment product through the ammonia gas suction unit 29.

Although there is no particular restriction on an ammonia separation unit 3, insofar as it can heat a presaccharification treatment product and evaporate ammonia gas, a unit with a heating multi-tube bundle, which rotates in a shell, is preferable, so as to perform efficiently in the ammonia separation unit 3 contact between a presaccharification treatment product and a heating tube bundle, and evaporation of ammonia in the presaccharification treatment product. For example, a continuous conduction heat dryer (e.g., Trade name: Inner Tube Rotary, made by Okawara Mfg. Co., Ltd.) can be used.

Then, a presaccharification treatment product from which ammonia has been separated out by the ammonia separation unit 3 is discharged by the discharging unit 31 from the ammonia separation unit 3, and transferred to a subsequent enzymatic saccharification step by the transfer unit 4.

REFERENCE SIGNS LIST

1: Pretreatment device for lignocellulosic biomass, 2: Treatment unit, 3: Ammonia separation unit, 21: Treatment vessel, 22: Substrate supply unit, 23: Ammonia water supply unit

The invention claimed is:

1. A presaccharification treatment device for lignocellulosic biomass comprising:
    a treatment unit configured to mix lignocellulosic biomass as a substrate and ammonia water, and then treat the yielded substrate mixture in a wet powder state to dissociate lignin contained in the substrate or to swell the substrate to yield a presaccharification treatment product in a wet powder state; and
    an ammonia separation unit configured to separate ammonia from the presaccharification treatment product;
    wherein the treatment unit comprises:
    a treatment vessel;
    a substrate supply unit configured to supply continuously the substrate to the treatment vessel;
    an ammonia water supply unit configured to supply continuously the ammonia water to the treatment vessel;
    a mixing unit configured to agitate the substrate and the ammonia water supplied to the treatment vessel to thereby apply shearing force and impact force to the substrate and to mix the ammonia water and the substrate to yield the substrate mixture; and
    a storage unit placed directly beneath the treatment vessel communicating with the treatment vessel and configured to store a substrate mixture supplied from the treatment vessel for a predetermined time period and to dissociate lignin contained in the substrate or to swell the substrate during storage without heating to yield a presaccharification treatment product; and
    wherein the ammonia separation unit comprises a presaccharification treatment product supply unit placed beneath the storage unit and configured to supply continuously the presaccharification treatment product from the storage unit to the ammonia separation unit, and is located directly beneath the storage unit.

2. The presaccharification treatment device for lignocellulosic biomass according to claim 1, wherein the ammonia water supply unit supplies ammonia water at a concentration in a range of 20 to 30% by mass, and supplies the ammonia water at a mass ratio in a range of 1:0.7 to 1:1.3 with respect to the substrate supplied by the substrate supply unit.

3. The presaccharification treatment device for lignocellulosic biomass according to claim 1;
    wherein the ammonia separation unit heats the presaccharification treatment product by a heating medium to separate ammonia from the presaccharification treatment product; and
    the presaccharification treatment product and the heating medium flow in the ammonia separation unit in a counter current direction.

4. The presaccharification treatment device for lignocellulosic biomass according to claim 1;

wherein the ammonia separation unit comprises:
an ammonia gas suction unit configured to suck ammonia gas vaporized from the presaccharification treatment product supplied into the ammonia separation unit; and
a vacuum-retaining unit configured to be able to maintain the presaccharification treatment product moving in the ammonia separation unit under a vacuum state by sucking the ammonia gas using the ammonia gas suction unit; and
wherein the vacuum-retaining unit comprises:
an introducing unit configured to maintain the presaccharification treatment product in the ammonia separation unit under a vacuum state, and to introduce the presaccharification treatment product supplied from the storage unit into the ammonia separation unit; and
a discharging unit configured to maintain the presaccharification treatment product in the ammonia separation unit under a vacuum state, and to discharge the presaccharification treatment product from which ammonia has been separated out from the ammonia separation unit.

* * * * *